United States Patent
Sly et al.

(10) Patent No.: US 10,997,444 B2
(45) Date of Patent: *May 4, 2021

(54) USE OF HUMAN INPUT RECOGNITION TO PREVENT CONTAMINATION

(71) Applicant: Medivators Inc., Minneapolis, MN (US)

(72) Inventors: Ward Sly, Brooklyn Park, MN (US); Stacy Lemmer, Minneapolis, MN (US); Terry Mistalski, Marine on St. Croix, MN (US); Michael Petersen, Eden Prairie, MN (US)

(73) Assignee: Medivators Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/592,279

(22) Filed: Oct. 3, 2019

(65) Prior Publication Data
US 2020/0029795 A1    Jan. 30, 2020

Related U.S. Application Data

(60) Division of application No. 16/115,173, filed on Aug. 28, 2018, now Pat. No. 10,588,492, which is a
(Continued)

(51) Int. Cl.
*G06F 3/00* (2006.01)
*G06F 3/01* (2006.01)
(Continued)

(52) U.S. Cl.
CPC ...... *G06K 9/00892* (2013.01); *A61B 1/00142* (2013.01); *A61B 1/04* (2013.01);
(Continued)

(58) Field of Classification Search
CPC .... G06F 3/0488; G06F 3/04883; G06F 3/044; G06F 3/04886; G06F 3/045; G06F 3/005
See application file for complete search history.

(56) References Cited

U.S. PATENT DOCUMENTS

| | | | | |
|---|---|---|---|---|
| 5,970,457 A | * | 10/1999 | Brant | A61B 17/00 704/275 |
| 7,893,842 B2 | | 2/2011 | Deutsch | |

(Continued)

FOREIGN PATENT DOCUMENTS

| | | |
|---|---|---|
| CN | 101344916 A | 1/2009 |
| CN | 104081411 A | 1/2014 |

(Continued)

OTHER PUBLICATIONS

"U.S. Appl. No. 14/372,178, Examiner Interview Summary dated Nov. 24, 2015", 3 pgs.
(Continued)

*Primary Examiner* — Md Saiful A Siddigui
(74) *Attorney, Agent, or Firm* — Schwegman Lundberg & Woessner, P.A.

(57) ABSTRACT

Embodiments of a system and method for processing and recognizing non-contact types of human input to prevent contamination are generally described herein. In example embodiments, human input is captured, recognized, and used to provide active input for control or data entry into a user interface. The human input may be provided in variety of forms detectable by recognition techniques such as speech recognition, gesture recognition, identification recognition, and facial recognition. In one example, the human input recognition techniques are used in connection with a device cleaning workflow used to obtain data and human input during cleaning procedures while minimizing cross-contamination between the contaminated device or person and other objects or persons. In another example, the human
(Continued)

input recognition techniques are used in connection with a device tracking workflow used to obtain data and human input while tracking interactions with and locations of the contaminated or uncontaminated device.

25 Claims, 8 Drawing Sheets

Related U.S. Application Data continuation of application No. 15/622,765, filed on Jun. 14, 2017, now Pat. No. 10,085,619, which is a continuation of application No. 15/143,023, filed on Apr. 29, 2016, now Pat. No. 9,681,794, which is a continuation of application No. 14/372,178, filed as application No. PCT/US2013/021547 on Jan. 15, 2013, now Pat. No. 9,361,530.

(60) Provisional application No. 61/588,980, filed on Jan. 20, 2012.

(51) Int. Cl.

| | | |
|---|---|---|
| *G06F 3/03* | (2006.01) | |
| *G06F 3/0484* | (2013.01) | |
| *G06F 3/16* | (2006.01) | |
| *A61B 1/00* | (2006.01) | |
| *A61B 1/12* | (2006.01) | |
| *G10L 17/24* | (2013.01) | |
| *G06K 9/00* | (2006.01) | |
| *G16H 40/20* | (2018.01) | |
| *A61B 1/04* | (2006.01) | |
| *A61B 90/70* | (2016.01) | |
| *G16H 40/40* | (2018.01) | |

(52) U.S. Cl.
CPC .............. *A61B 1/121* (2013.01); *A61B 90/70* (2016.02); *G06F 3/005* (2013.01); *G06F 3/017* (2013.01); *G06F 3/0304* (2013.01); *G06F 3/04842* (2013.01); *G06F 3/167* (2013.01); *G10L 17/24* (2013.01); *G16H 40/20* (2018.01); *A61B 2090/701* (2016.02); *G16H 40/40* (2018.01)

(56) References Cited

U.S. PATENT DOCUMENTS

| | | | |
|---|---|---|---|
| 8,992,837 | B2 | 3/2015 | Jung et al. |
| 9,361,530 | B2 | 6/2016 | Sly et al. |
| 9,681,794 | B2 | 6/2017 | Sly et al. |
| 10,085,619 | B2 | 10/2018 | Sly et al. |
| 2004/0091389 | A1 | 5/2004 | Malkin et al. |
| 2005/0065405 | A1 | 3/2005 | Hasegawa |
| 2005/0149530 | A1 | 7/2005 | Oswal |
| 2006/0142739 | A1 | 6/2006 | Disilestro et al. |
| 2007/0139202 | A1* | 6/2007 | Austin ............... G06Q 10/08 340/572.8 |
| 2008/0081956 | A1 | 4/2008 | Shah et al. |
| 2008/0082339 | A1 | 4/2008 | Li et al. |
| 2009/0089093 | A1 | 4/2009 | Johnson et al. |
| 2009/0182577 | A1 | 7/2009 | Squilla et al. |
| 2009/0282371 | A1 | 11/2009 | Curl |
| 2010/0131280 | A1 | 5/2010 | Bogineni |
| 2010/0217620 | A1 | 8/2010 | Kippenhan et al. |
| 2011/0157480 | A1 | 6/2011 | Curl |
| 2011/0172994 | A1 | 7/2011 | Lindahl et al. |
| 2011/0316695 | A1 | 12/2011 | Li et al. |
| 2012/0066600 | A1 | 3/2012 | Nickel |
| 2012/0073614 | A1* | 3/2012 | Otani ............... A61B 1/121 134/56 R |
| 2012/0217184 | A1 | 8/2012 | Edwards et al. |
| 2012/0323597 | A1 | 12/2012 | Woolford |
| 2013/0176220 | A1 | 7/2013 | Merschon et al. |
| 2013/0225999 | A1 | 8/2013 | Banjanin et al. |
| 2015/0109193 | A1 | 4/2015 | Sly et al. |
| 2016/0235280 | A1 | 8/2016 | Sly et al. |
| 2017/0273547 | A1 | 9/2017 | Sly et al. |
| 2019/0008366 | A1 | 1/2019 | Sly et al. |

FOREIGN PATENT DOCUMENTS

| | | |
|---|---|---|
| CN | 104081411 B | 12/2017 |
| WO | WO-2013109525 A1 | 7/2013 |

OTHER PUBLICATIONS

"U.S. Appl. No. 14/372,178, Non Final Office Action dated Aug. 17, 2015", 22 pgs.
"U.S. Appl. No. 14/372,178, Notice of Allowance dated Mar. 3, 2016", 10 pgs.
"U.S. Appl. No. 14/372,178, Preliminary Amendment filed Jul. 14, 2014", 9 pgs.
"U.S. Appl. No. 15/143,023, Non Final Office Action dated Dec. 16, 2016", 10 pgs.
"U.S. Appl. No. 15/143,023, Notice of Allowance dated Feb. 21, 2017", 5 pgs.
"U.S. Appl. No. 15/143,023, Response filed Jan. 13, 2017 to Non Final Office Action dated Dec. 16, 2016", 9 pgs.
"U.S. Appl. No. 15/622,765, Examiner Interview Summary dated Jun. 14, 2018", 3 pgs.
"U.S. Appl. No. 15/622,765, Non Final Office Action dated Mar. 8, 2018", 36 pgs.
"U.S. Appl. No. 15/622,765, Notice of Allowance dated Jul. 17, 2018", 8 pgs.
"U.S. Appl. No. 15/622,765, Preliminary Amendment filed Jun. 15, 2017", 9 pgs.
"U.S. Appl. No. 15/622,765, Response filed Jun. 8, 2018 to Non Final Office Action dated Mar. 8, 2018", 16 pgs.
"U.S. Appl. No. 16/115,173, Non Final Office Action dated Jul. 11, 2019", 31 pgs.
"U.S. Appl. No. 16/115,173, Preliminary Amendment filed Aug. 28, 2018", 8 pgs.
"U.S. Appl. No. 16/115,173, Supplemental Preliminary Amendment filed Aug. 29, 2018", 9 pgs.
"U.S. Appl. No. 14/372,178, Response filed Nov. 17, 2015 to Non-Final Office Action dated Aug. 17, 2015", 15 pgs.
"U.S. Appl. No. 15/143,023, Preliminary Amendment filed May 2, 2016", 10 pgs.
"Chinese Application Serial No. 201380006063.1, Office Action dated May 17, 2017", with English Translation, 6 pgs.
"Chinese Application Serial No. 201380006063.1, Office Action dated Sep. 30, 2016", w/English Translation, 23 pgs.
"Chinese Application Serial No. 201380006063.1, Response filed Feb. 15, 2017 to Office Action dated Sep. 30, 2016", With English Claims, 48 pgs.
"Chinese Application Serial No. 201380006063.1, Response Filed Aug. 1, 2017 to Office Action dated May 17, 2017", With English Claims, 20 pgs.
"European Application Serial No. 13739096.9, Communication Pursuant to Article 94(3) EPC dated Dec. 6, 2018", 6 pgs.
"European Application Serial No. 13739096.9, Extended European Search Report dated Apr. 22, 2016", 6 pgs.
"European Application Serial No. 13739096.9, Response filed Jun. 14, 2019 to Communication Pursuant to Article 94(3) EPC dated Dec. 6, 2018", 19 pgs.
"European Applicatien Serial No. 13739096.9, Office Action dated Sep. 2, 2014", 3 pgs.
"European Application Serial No. 13739096.9, Response filed Nov. 18, 2016 to Extended European Search Report dated Apr. 22, 2016", 22 pgs.
"International Application Serial No. PCT/US2013/021547, Internatiional Preliminary Report on Patentability dated Jul. 31, 2014", 8 pgs.

(56) References Cited

OTHER PUBLICATIONS

"International Application Serial No. PCT/US2013/021547, International Search Report dated Mar. 22, 2013", 2 pgs.

"International Application Serial No. PCT/US2013/021547, Written Opinion dated Mar. 22, 2013", 6 pgs.

"European Application Serial No. 13739096.9, Communication Pursuant to Article 94(3) EPC date Sep. 22, 2020", 6 pgs.

U.S. Appl. No. 14/372,178, filed Jul. 14, 2014, U.S. Pat. No. 9,361,530, Use of Human Input Recognition to Prevent Contamination.

U.S. Appl. No. 15/143,023, filed Apr. 29, 2016, U.S. Pat. No. 9,681,794 Use of Human Inpur Recognition to Prevent Contamination.

U.S. Appl. No. 15/622,765, filed Jun. 14, 2017, U.S. Pat. No. 10,085,619, Use of Human Input Recognition to Prevent Contamination.

U.S. Appl. No. 16/115,173, filed Aug. 28, 2018, Use of Human Input Recognition to Prevent Contamination.

* cited by examiner

USE OF HUMAN INPUT RECOGNITION TO PREVENT CONTAMINATION

PRIORITY CLAIM

This application is a division of U.S. patent application Ser. No. 16/115,173, filed on Aug. 28, 2018, which is a continuation of U.S. patent application Ser. No. 15/622,765, filed on Jun. 14, 2017, which is a continuation of U.S. patent application Ser. No. 15/143,023, filed on Apr. 29, 2016, which is a continuation of U.S. patent application Ser. No. 14/372,178, filed on Jul. 14, 2014, which is a United States National Stage Filing Under 35 U.S.C. § 371 from International Patent Application No. PCT/US2013/021547, filed on Jan. 15, 2013, which claims the benefit of priority to U.S. Provisional Patent Application Ser. No. 61/588,980, filed on Jan. 20, 2012, titled "USE OF HUMAN INPUT RECOGNITION TO PREVENT CONTAMINATION," the disclosures of each of which are incorporated herein by reference in their entireties.

TECHNICAL FIELD

Embodiments pertain to the use of human input recognition methods and techniques. Some embodiments relate to techniques and configurations for recognizing and processing human input in contamination settings, such as in connection with the use of medical devices and systems.

BACKGROUND

Unintended contamination of objects may occur in a variety of industrial, scientific, or medical settings. In a medical setting, for example, specific contamination precautions must be undertook when cleaning reusable medical equipment. As one example in the medical setting involving reusable medical equipment, endoscopes that are designed for use in multiple procedures must be fully cleaned and reprocessed after a medical procedure to prevent the spread of infectious organisms. Once an endoscope is used in the medical procedure, the endoscope is considered contaminated until it is properly cleaned and disinfected.

Various systems and protocols are used to ensure suitable cleaning and disinfection of endoscopes. For example, machines and devices such as automated endoscope reprocessors are used to perform machine cleaning of an endoscope. As part of a proper cleaning protocol, the machines and devices responsible for the cleaning often require human control and oversight. However, during the cleaning process, any person handling a contaminated endoscope, and all protective gear of the person, is considered contaminated once the person has initiated contact with the contaminated equipment. This may result in the machines, devices, or any other object exposed to human contact also becoming contaminated, resulting in various cross-contamination problems if proper cleaning of these objects is not undertaken. Therefore, there is a general need to reduce human contact with contaminated equipment during cleaning processes, as well as a general need to prevent human contact with non-contaminated equipment once a person becomes contaminated.

DETAILED DESCRIPTION

Figure 1:
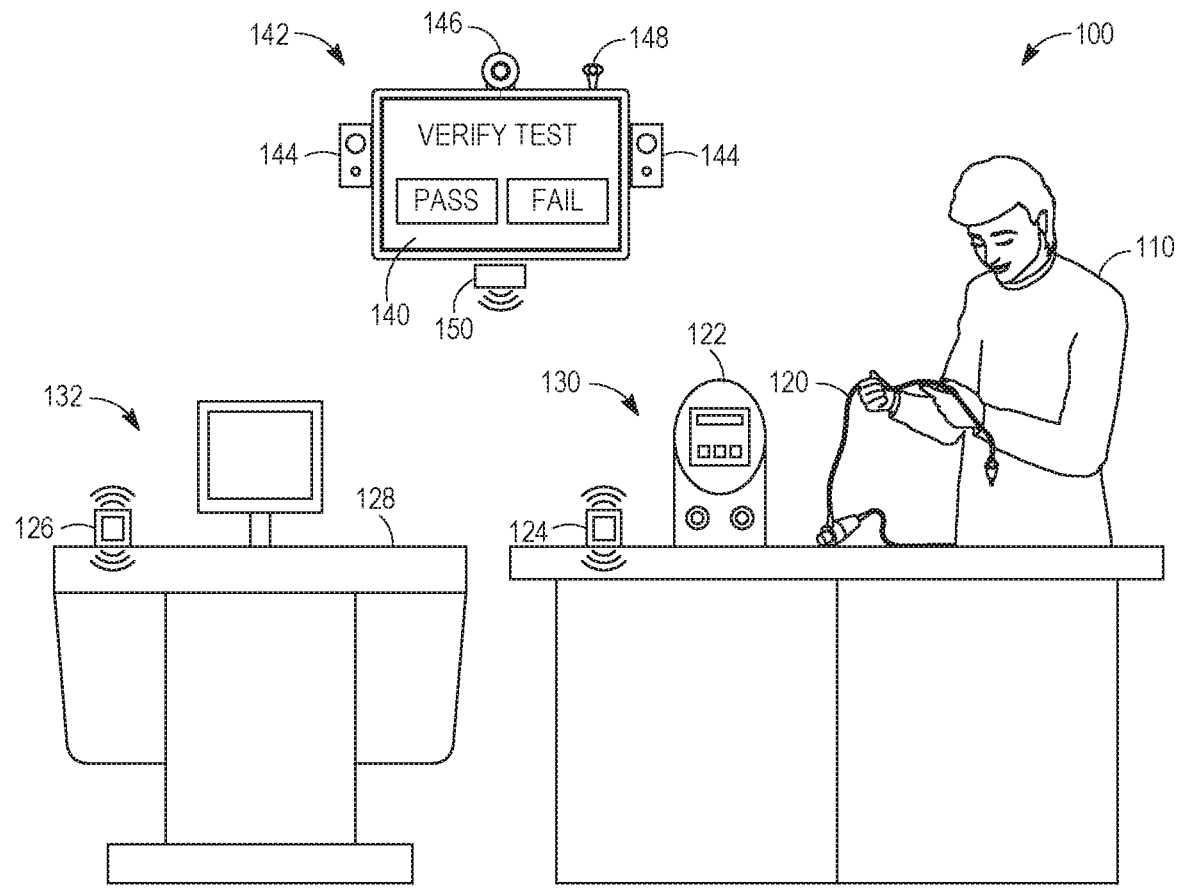
FIG. 1 provides an illustration of a human input recognition scenario in a medical contamination setting in accordance with example embodiments.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Various techniques for detecting, determining, and accepting human input in a contamination-sensitive or other controlled setting are described herein. These techniques for detecting, determining, and accepting active input from a human may include any combination of speech recognition, identifier recognition, facial recognition, gesture recognition, wireless and near field communication, and like techniques to obtain information offered from a human without direct human contact. As referred to herein, such active input which may take any of a number of forms is generally referred to as "non-contact human input." The non-contact human input that is obtained from the human may be used to control a single or multiple of machines, devices, computing systems, and like electronic or mechanical apparatuses.

In one example embodiment, the human input is detected in a contamination-sensitive medical setting to avoid contamination and cross-contamination between a contaminated object and one or more other objects or humans. Likewise, the human input may be detected to avoid contamination being conveyed from a person considered contaminated (such as by a person wearing contaminated protective gear or previously handling contaminated objects) to other objects or humans.

Therefore, the presently described techniques and configurations may allow human input to be recognized and processed without direct human touch or contact with an input device. A machine which requires user input with a touchscreen, mouse, keyboard, or other contact-driven input device also requires human contact to control such input device. This introduces the potential of contamination if a human who is considered contaminated needs to provide the machine with active user input. Likewise, a human who is overseeing a process involving a contaminated object may not want to interact with an input device if such interaction introduces the potential of becoming contaminated from the input device.

As further described herein, non-contact human input may be detectable in connection with a variety of recognition techniques including but not limited to speech recognition, identifier recognition, gesture recognition, facial recognition, and wireless and near field communication. As also further described herein, the system prompts used to elicit such non-contact human input may be provided using any number of human-detectable outputs, including one or more displays, audio outputs (including text-to-speech capabilities from a computing system), or other suitable indicators that prompt a user to provide human input. In some examples, the non-contact human input may be collected and recognized in order to control the display of a graphical user interface; in other examples, the non-contact human input is provided to directly obtain input for electronic devices or machines, and does not involve control of a graphical user interface with the non-contact human input.

FIG. 1 provides an illustration of an example system configured to perform human input recognition techniques in a contamination-sensitive environment, such as a medical device cleaning environment. In the environment 100 illustrated in FIG. 1, a human user 110 performs one or more operations, for example, cleaning operations, in connection with a contaminated object such as a medical device. The contaminated medical device, specifically illustrated in FIG. 1 as an endoscope 120, is handled by human user 110 at one or both of manual cleaning station 130 or automated cleaning station 132. The manual cleaning station 130 may include, for example, a sink used to perform manual cleaning of visible debris upon the endoscope 120, and a flushing aid 122 used to perform manual channel flushing operations with the endoscope 120. The automated cleaning station 132 may include, for example, an automatic endoscope reprocessor 128 configured to perform automated chemical disinfection upon the endoscope 120.

In connection with operations at the manual cleaning station 130 or the automated cleaning station 132, a cleaning or contamination status of the endoscope 120 may be tracked. This may be performed in connection with a tracking identifier unique to the endoscope 120, such as a barcode, RFID tag, or other identifier coupled to the endoscope 120. As illustrated, the manual cleaning station 130 and the automated cleaning station 132 each provide an identifier detector 124, 126 respectively to perform identification of the particular endoscope being cleaned at the respective cleaning station. In one embodiment, the identifier detector 124, 126 comprises a RFID interrogator or reader used to perform touch-free identification of an endoscope's unique tracking identifier. Tracking locations of the endoscope 120 and activities performed with the endoscope 120 based on its unique tracking identifier may be performed in connection with a device handling workflow such as a cleaning workflow or a tracking workflow, as further described herein.

In connection with a cleaning workflow, tracking workflow, or other suitable device handling workflow which manages or tracks operations occurring in the contamination-sensitive environment, a user interface 140 is presented to the human user 110 via a display device 142. For example, the user interface 140 may request input from the human user 110 to verify whether a particular cleaning protocol has been followed by the human user 110 at each of the manual cleaning station 130 and the automated cleaning station 132.

Thus, specific inquiries, prompts, or collections of data may occur at various points in the cleaning or tracking workflow to collect relevant data. Such collections of data may be offered for procedure validation or quality assurance purposes, for example, to obtain human verification that a cleaning process has followed proper protocols, or that human oversight of the cleaning process has resulted in a satisfactory result. Workflow steps may also be required to be performed in a determined order to ensure proper cleaning, and therefore user inquiries and prompts may be presented in a determined order to collect full information regarding compliance or procedure activities.

As illustrated, the user interface 140 may be provided by the display device 142 in viewing range of the human user 110. Alternatively or in combination with the display device 142, a set of audio indications may be played to the human user 110 through one or more speakers 144. For example, one or more system-determined messages corresponding to text and selectable options displayed within the user interface 140 may be output to the human user 110 through the speakers 144.

The human input from the human user 110 may be obtained and recognized from any number of input forms. For example, a camera 146 operably coupled to the user interface 140 may capture video or a series of images of the human user 110 to determine gesture commands acted out by the human user 110. As another example, a microphone 148 may capture audio of the human user 110 to determine speech recognition commands verbalized by the human user 110. As yet another example, the camera 146 may be used in connection with facial recognition, such as the movement of a cursor in user interface 140 based on the detected eye focus of the human user 110 upon the display device 142. As another example, the camera 146, a near field communication component 150, or an external barcode reader (not shown) may be used in connection with identifier recognition, such as the detection of a barcode or RFID identifier being provided by a user in response to an inquiry displayed in the user interface 140.

The user interface 140 may be configured to enable control by other human user input devices, such as a keyboard or a mouse (not shown), touchscreen capabilities within the display device 142, and like devices which require human contact for operation. However, in a contamination-sensitive environment, the use of such contact-driven input devices by a contaminated user may be not intended due to potential contamination of the input device. Likewise, if the human user is not currently contaminated and is considered to be clean, then the human user may intend to avoid potential contamination from direct contact with such contact-driven input devices.

Figure 2:
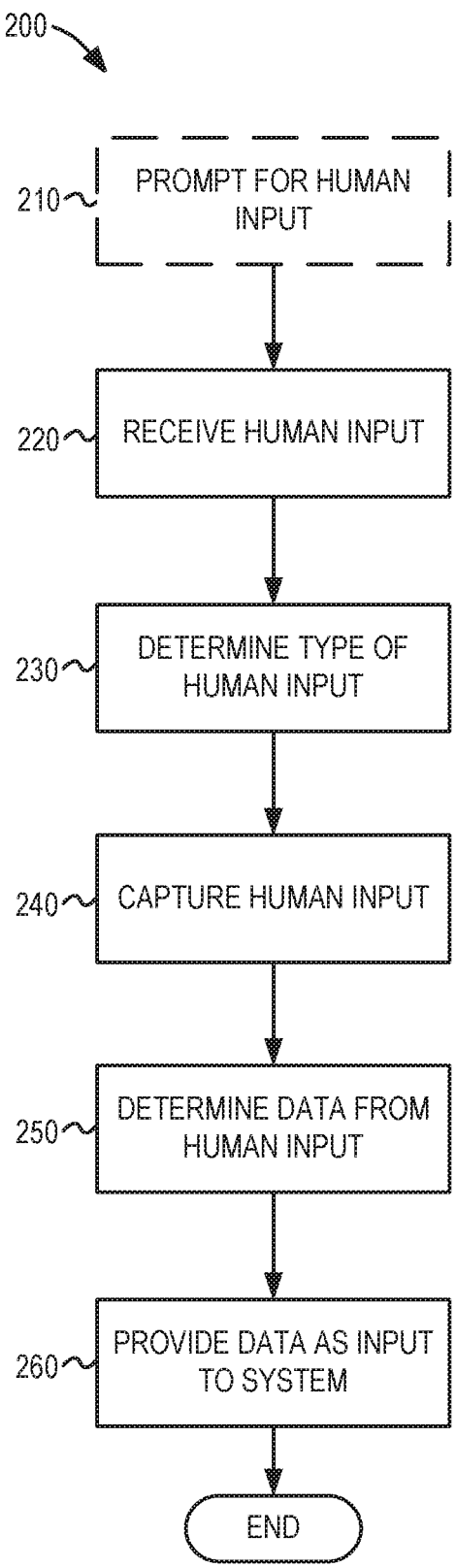
FIG. 2 illustrates a flowchart providing an overview of human input capture and recognition in accordance with example embodiments.

FIG. 2 illustrates a flowchart 200 providing an overview of an example human input collection method conducted in connection with one or more embodiments. As illustrated, a series of operations result in the collection of data in response to human input. It will be apparent that the order and result of these operations may vary depending on the type of human input, and the type of command resulting from the human input.

As shown, a prompt for human input may be provided (operation 210). The prompt may be provided in connection with user-selectable options or verification procedures. The prompt may be optional, however, in certain contexts. For example, active human input in the form of user-initiated commands may be used to provide input that is not directly responsive to a user prompt (for example, an "abort" verbal command issued from a user to interrupt an ongoing procedure). Whether provided in response to a prompt or not, the human input is received (operation 220).

Next, the particular type of received human input is determined (operation 230). In a setting where both audio and video input are obtained, such as in a combination of voice detection and gesture detection, data from various input devices such as video data and audio data may be processed to determine the context of specific audio or video input, and whether human input is provided. Next, the human input is captured (operation 240). A variety of recognition algorithms may be used, for example, to extract data from audio or video output. This may include capturing an audio sequence for speech recognition commands, capturing an outline of a person for gesture recognition commands, and the like.

The recognition algorithms may be used to capture a particular sequence or segment of data from the human input. The specific data is then determined from the human input (operation 250). For example, a recognition technique may be used to convert audio containing verbalized words into speech recognition data that is then provided as text in a user interface. Likewise, speech recognition may be used to correlate the audio containing the verbalized word "Fail" into a selectable "Fail" input choice being displayed by a user interface in a computing system. Likewise, gesture recognition may be used to correlate a gesture such as a user's arm being held at a certain position for a period of time into a confirmation or selection of an input choice being provided by a computing system.

Responsive to the data being determined from the human input, the data may be provided as input to a data-driven system (operation 260). For example, data may be provided in connection with inputs of a user interface being presented by a computer system or device. The data may also be used to initiate a command in a computer system or device. The data may also be communicated to one or more systems, such as a workflow system or tracking system configuration as further described herein.

Some of the human input recognition techniques that may be performed in connection with the use cases and system configurations described herein are described in the following techniques. Such techniques that are suited for recognition of non-contact input may be used separately or in combination with each other, and separately or in combination with certain contact-based human input techniques in appropriate settings.

Speech recognition in connection with the human input techniques described herein may include the recognition of language-specific words into specific commands or word-based data for input into a computing system or other electronic device. The speech recognition may be used in connection with a voice user interface which prompts a user for input. With such an example, a system which asks "Is cleaning now complete?" may be configured to recognize the verbal commands "Yes" or "No" spoken from a user. Likewise, a system may process verbal commands spoken from a user such as "Stop", "Start", "Abort", and the like which may not be provided in response to a prompt from a voice user interface. Speech recognition may also be used in connection with data entry from a human user, such as to provide speech-to-text processing of a human-spoken narrative to collect relevant information.

In a further embodiment, the speech recognition may be specific to one or more users, in connection with voice recognition technology designed to recognize voices of one or more specific users. For example, a speech recognition system may be trained to only identify a selected voice, to prevent other voices (for example, from multiple voices in a crowded room) from providing unintended input or control.

Speech recognition may be provided using any number of custom or preprogrammed automated speech recognition capabilities provided from a standalone machine, operating system, or software application. For example, speech recognition capabilities such as Windows Speech Recognition provided by the Windows operating system may be used to translate verbal commands into human input for a graphical user interface being displayed by the operating system. Moreover, speech recognition and control by user verbal commands may be used to provide control with any permutation of human-computer interfaces, such as a voice user interface accepting commands in combination with a touchscreen user interface display.

Identifier recognition in connection with the human input techniques described herein may include a computer-derived recognition of identifiers used to provide responses to certain commands. For example, a user may provide one of two barcodes, one representing "pass" and one representing "fail", to respond to an inquiry from a system. Such barcodes may be provided on handheld cards or objects handled by the human user. A user may select one of the two cards in response to the inquiry, and a laser-operated barcode reader may be used to obtain an identifier correlating to the response without making contact with the contaminated person or object. Because a barcode identifier simply requires a display of printed information, the barcode may be provided on a variety of low-cost and disposable media. In another example, the barcode identifier may be printed onto the object being handled, or onto protective clothing of the operator handling the object.

Other types of identifiers may be detected in connection with non-contact identifier recognition techniques. For example, a camera may capture an image that is used to detect a red-colored object presented by a user that represents a "fail" identifier, versus a green-colored object presented by a user that represents a "pass" identifier. Likewise, other types of remotely-readable identifiers provided from near field communication objects such as RFID tags may be used by a human user to provide active input with a RFID reader.

Gesture recognition in connection with the human input techniques described herein may include a computer-derived recognition of specific human gestures using cameras and computer vision algorithms to interpret predetermined gestures. For example, a camera operably coupled to a computer-operated gesture recognition system may be used to detect a human interaction at a certain location, such as a user raising or holding his or her arm at a certain angle, or a user providing a series of detectable motions. The gesture recognition technique may be provided in combination with a display that projects the placement of the human user in some space and enables the human user to perceive the detection of the gestures.

Gesture recognition may be provided using any number of custom or preconfigured gesture detection components provided from a standalone machine, operating system, software application, or combination thereof. For example, gesture detection provided in connection with a Microsoft Kinect for Windows hardware sensor unit and recognition software may be used in connection with a software application operating on a Windows operating system to perform human tracking, gesture recognition, and voice control. In another example, a wand or other motion controller may be used in connection gesture recognition techniques to provide more accurate control of a gesture-based user interface.

Facial recognition in connection with the present human input recognition techniques described herein may include the recognition of facial gestures, eye tracking, and other non-verbal cues specific to the face of a user. In one embodiment, tracking of a user's eye focus may be used to control cursor motion based on the detected location of a user's eye as compared with a defined location. Eye tracking may be combined with certain detection algorithms to enable user interface interaction, such as providing a selection with a cursor if a user focuses his or her eye on an interface selection display for at least a predefined period of time (looking at a button for at least three seconds, as one non-limiting example). In another embodiment, face-based gestures such as facial expressions (for example, a "surprised" or "confused" look detected from a human) ay be used perform commands such as stopping a machine.

In one embodiment, the facial recognition and gesture recognition techniques may be tailored to perform recognition from persons who are wearing protective clothing or other protective gear which may obscure all or portions of the user's face. Likewise, speech recognition techniques may be tailored to perform speech recognition from persons who may have protective headwear or may not be able to clearly verbalize commands. Thus, the recognition techniques may be adapted to use in a specific contamination handling environment.

Figure 3:
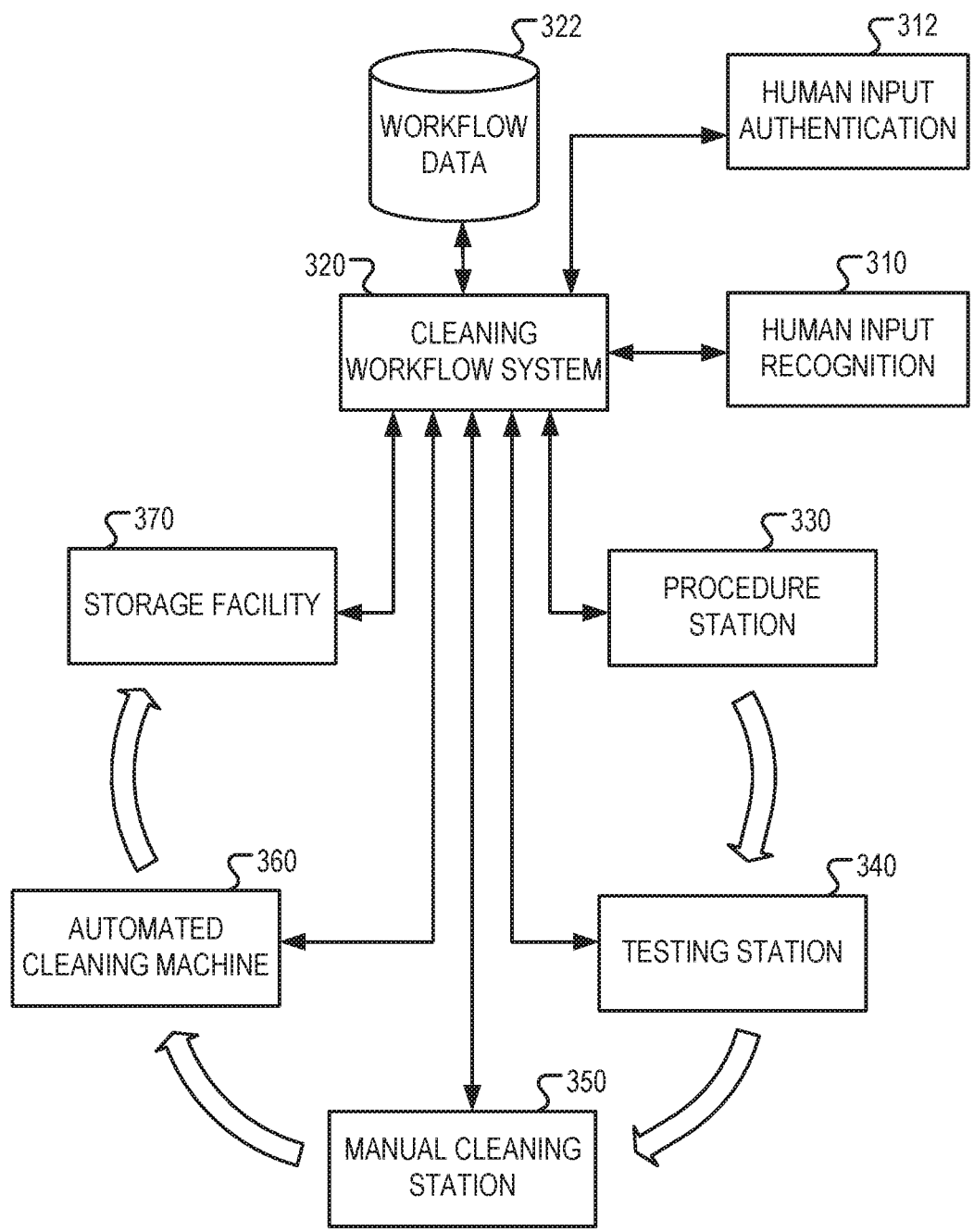
FIG. 3 is a block diagram of system components used to interface with a human input recognition component within a cleaning workflow in accordance with example embodiments.

As further described herein, these human input recognition techniques may be integrated in connection with the use of a cleaning workflow facilitated by an electronic cleaning workflow system. FIG. 3 provides a block diagram illustrating the interaction between various machines and components in connection with use of a cleaning workflow that is configured to perform human input recognition from non-contact methods of human input.

With reference to FIG. 3, various human input recognition activities (such as voice recognition, gesture recognition, and facial recognition) may be facilitated by a human input recognition component 310. The human input recognition component 310 is operably coupled to a cleaning workflow system 320. The cleaning workflow system 320 may include one or more computing systems configured to manage cleaning activities of one or more identifiable objects (such as identified medical devices) in a contamination environment. In an alternate embodiment, the human input recognition component 310 may be directly provided within logic or devices of the cleaning workflow system 320.

Appropriate identification, verification, security, or like authentication techniques may be facilitated by a human input authentication component 312, for example, to positively identify the human user of a machine or device in the cleaning workflow system 320. The cleaning workflow system 320 may be operably coupled to communicate with the human input authentication component 312, and facilitate an authentication process in response to certain human input processed by the human input recognition component 310. In an alternative embodiment, the human input provided from the human input recognition component 310 may be directly provided to the human input authentication component 312.

The cleaning workflow system 320 is configured to store workflow data in a workflow data store 322. For example, the cleaning workflow may track data for a plurality of identifiable objects at each stage of the cleaning workflow, and may further track data related to the activities performed at each stage of the cleaning workflow. The cleaning workflow system 320 may further collect human input at each stage of the cleaning workflow in connection with one or more user interfaces, user prompts, or interactions with a human user.

The cleaning workflow system 320 may be operably coupled to communicate with individual devices, systems, or stations which perform specific types of cleaning actions. Such communications may be facilitated with a procedure station 330, a testing station 340, a manual cleaning station 350, an automated cleaning machine 360, and a storage facility 370. For example, the cleaning workflow system 320 may maintain workflow data for a specific identifiable object as the identifiable object is being interacted with at each of these stations. The cleaning workflow system 320 may further capture human input using the human input recognition component 310, as a human user performs actions and oversees the operation of the identifiable object at each of the stations.

FIG. 3 further illustrates a series of arrows depicting a workflow which involves operations at each of the following stations. At the procedure station 330, the device may be used to conduct certain procedures that result in contamination (for example, an endoscopy procedure). Cleaning steps performed at the procedure station 330 may include basic protocols to wipe down the device and prepare the device for further cleaning. At the testing station 340, various tests may be performed to verify the operation or functionality of the device being cleaned. For example, in connection with testing of an endoscope device, leak testing may be performed to ensure that fluid damage will not occur during subsequent cleaning. If the endoscope fails this test, then it may be marked for service in the cleaning workflow. At the manual cleaning station 350, the device may be manually cleaned for debris according to certain human-performed procedures and protocols. At the automated cleaning machine 360, the device may be cleaned by an automated process according to machine-performed procedures. At the storage facility 370, the device may be stored once it is recognized as fully disinfected from contamination and in a sterile state.

Figure 4:
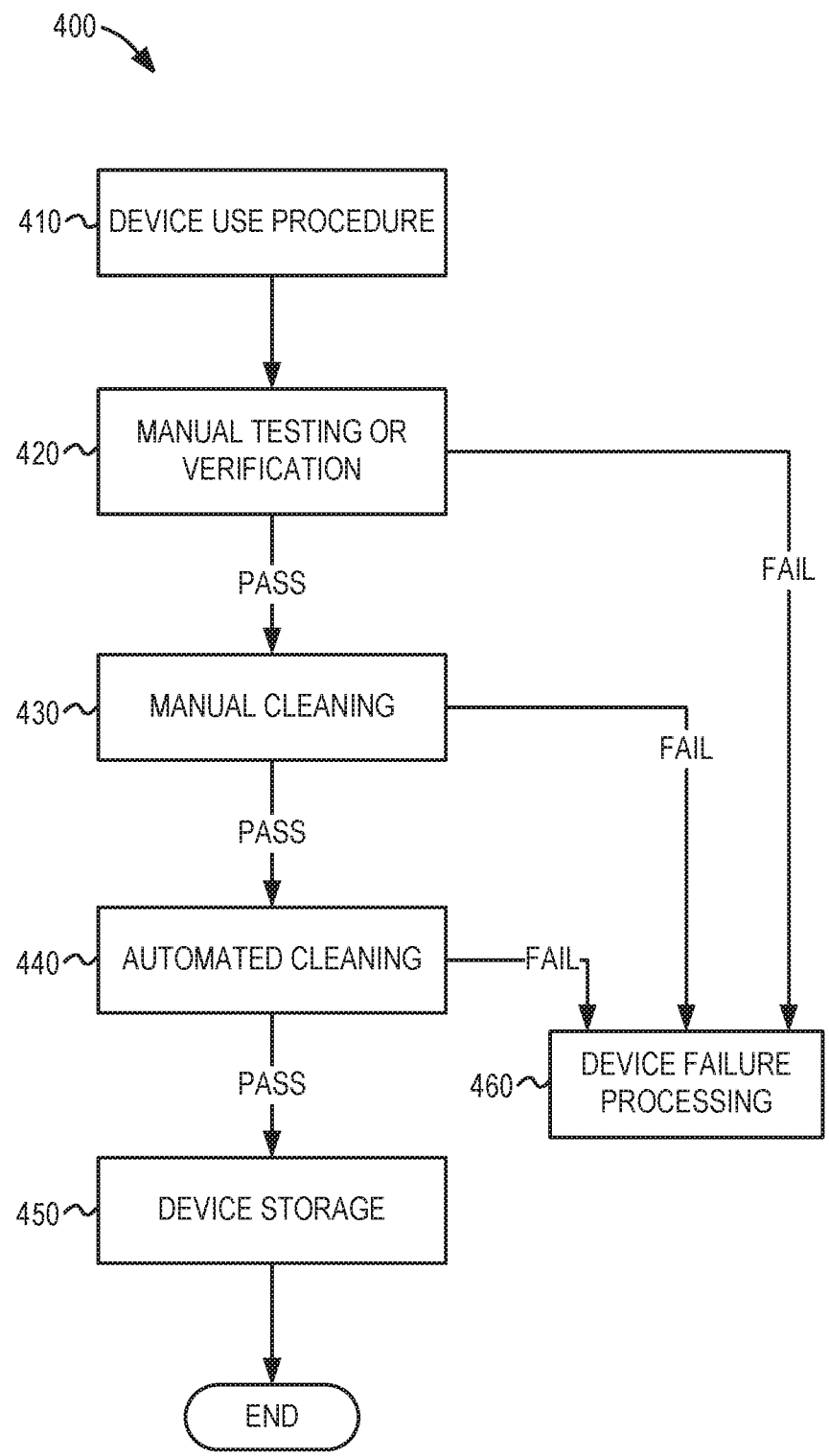
FIG. 4 illustrates a flowchart providing an overview of a device cleaning workflow conducted in accordance with example embodiments.

FIG. 4 illustrates a flowchart 400 providing an overview of an example device cleaning workflow conducted in connection with one or more embodiments. For example, the device cleaning workflow may be conducted in connection with the example cleaning workflow system configuration and components illustrated in FIG. 3.

As illustrated, use of the device occurs in the device use procedure (operation 410). For example, this may occur in connection with the use of a medical device (such as an endoscope) in a medical operation (such as an endoscopic procedure). Generally, as a result of the device use procedure, the device becomes contaminated. In some scenarios, however, the device may become contaminated independent of a device use procedure.

The next stage of the device cleaning workflow includes manual testing or verification (operation 420), such as may be performed by a human user. This may include requesting or receiving human user input in order to verify the results of the testing or verification. For example, a user may provide input to indicate whether a device has passed or failed a certain test (such as a leak test). If the test failed, device failure processing (operation 460) may occur to collect additional user input from the human regarding the test failure details, for example, details regarding any detected damage upon the device.

The next stage of the device cleaning workflow includes manual cleaning (operation 430), such as may be performed by a human user at a manual cleaning station according to a device manufacturer's instructions. This may include requesting or receiving human user input in order to verify operations related to human-initiated cleaning activities. Failure of this stage may also result in device failure processing (operation 460). For example, if a human recognizes that flushing of the endoscope at the cleaning station is not successful due to a failed channel, the blockage may be recorded in the device cleaning workflow. The human user may provide specific details on the particular failure in conjunction with particular endoscope being marked for repair.

The next stage of the device cleaning workflow includes automated cleaning (operation 440), such as may be performed at an automated cleaning machine such as an automated endoscope processor. This may include requesting or receiving human user input in order to verify operations and protocol from a human observer. For example, a human user may provide input to verify the disinfection concentration used in the automated endoscope reprocessor. Failure of this stage may also result in device failure processing (operation 460).

The final stage of the device cleaning workflow includes device storage (operation 450) for a non-contaminated device, for example as may be performed at a storage facility such as an endoscope storage cabinet. This may include receiving or recognizing human user input in connection with actions at a storage facility in order to verify that the human has handled the device properly according to protocol and has not introduced the potential of contamination.

In the device cleaning workflow, the successful disinfection of the device may not occur unless the workflow is followed in a complete fashion in the correct order. Various verification steps and quality assurance procedures may be performed in connection with the input recognition techniques described herein to ensure compliance and quality assurance. This may include verifying previous workflow steps with human input prior to continuing with the next workflow step. For example, manual cleaning may need to be completed and verified by a manual input from the human user prior to performing automated cleaning involving reprocessing or disinfection. A variety of automated checks and human verification prompts may be performed in connection with the device cleaning workflow to ensure that the steps of cleaning are carried out successfully and in the correct order. In one scenario, if a device skips full completion of any of the steps, an error message is generated to alert the operator and display appropriate prompts or information.

Additional stages or steps that require active human user input may be performed in connection with the device cleaning workflow. These may include manual pre-cleaning, wipe down, and flushing of the device prior to or in conjunction with the manual testing or verification process. Such manual activities may implicate receiving or requesting active human user input in order to validate that the manual activities were performed. Likewise, modifications may be made to the device cleaning workflow to handle human user input occurring responsive to specific conditions, such as failure conditions or abnormal conditions occurring in any of the workflow stages.

Figure 5:
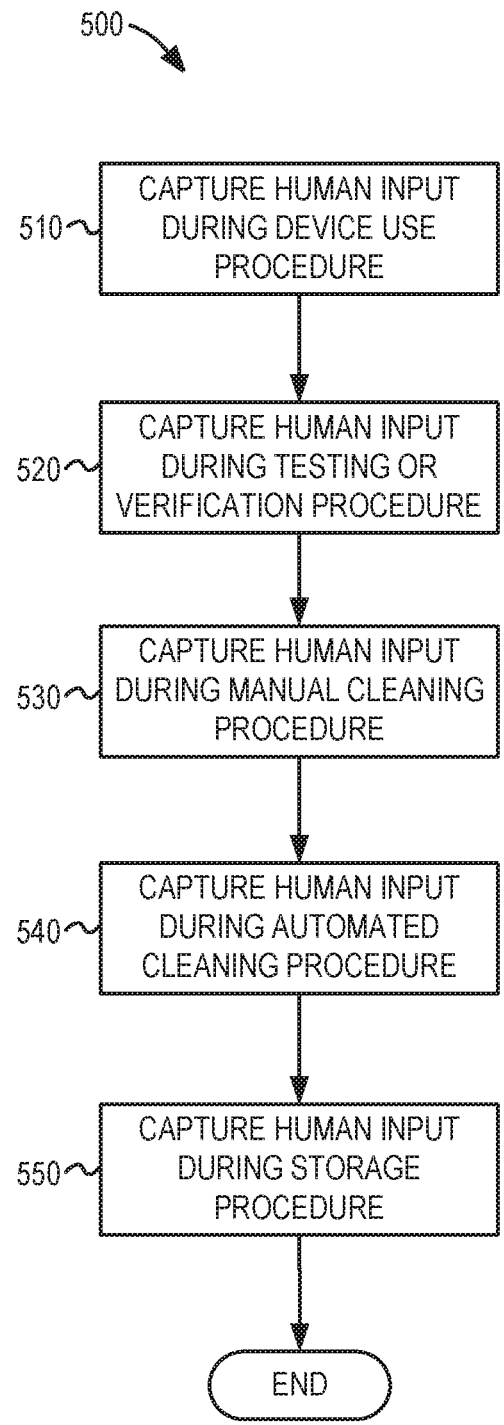
FIG. 5 illustrates a flowchart providing an overview of human input collected in connection with a device cleaning workflow conducted in accordance with example embodiments.

FIG. 5 illustrates a flowchart 500 providing an overview of human input collected in connection with a cleaning workflow (such as the device cleaning workflow illustrated in FIG. 4) performed in an example embodiment. As illustrated, human input may be captured during a device use procedure (operation 510). Typically the device use procedure (e.g., a medical procedure) is the point where the contamination is first introduced to the device, whereas the contamination is fully removed upon the successful completion of the automated cleaning (upon completion of operation 540). Therefore, subsequent human input in the cleaning workflow is used to minimize contact between a contaminated person or object with non-contaminated objects and persons, including potential contamination that might occur during or after the workflow.

As further illustrated in FIG. 5, human input may be captured during a testing or verification procedure (operation 520); during a manual cleaning procedure (operation 530); during an automated cleaning procedure (operation 540); and during a storage procedure (operation 550). For example, during a testing procedure, the system may capture voice inputs from the user provided in response to human verification needed for each test performed and the outcome of the test. Human input may also be captured in connection with other procedures or in response to other external conditions during the workflow.

In one embodiment, steps performed within a medical device cleaning workflow may be performed or validated in part or in whole using the human input recognition techniques described herein. Human input provided in connection with the performance of a cleaning workflow may be used to provide any number of commands or data inputs. As also described herein, various human input recognition techniques may be integrated in connection with the use of a device or object tracking workflow provided in connection with a device or object tracking system.

Figure 6:
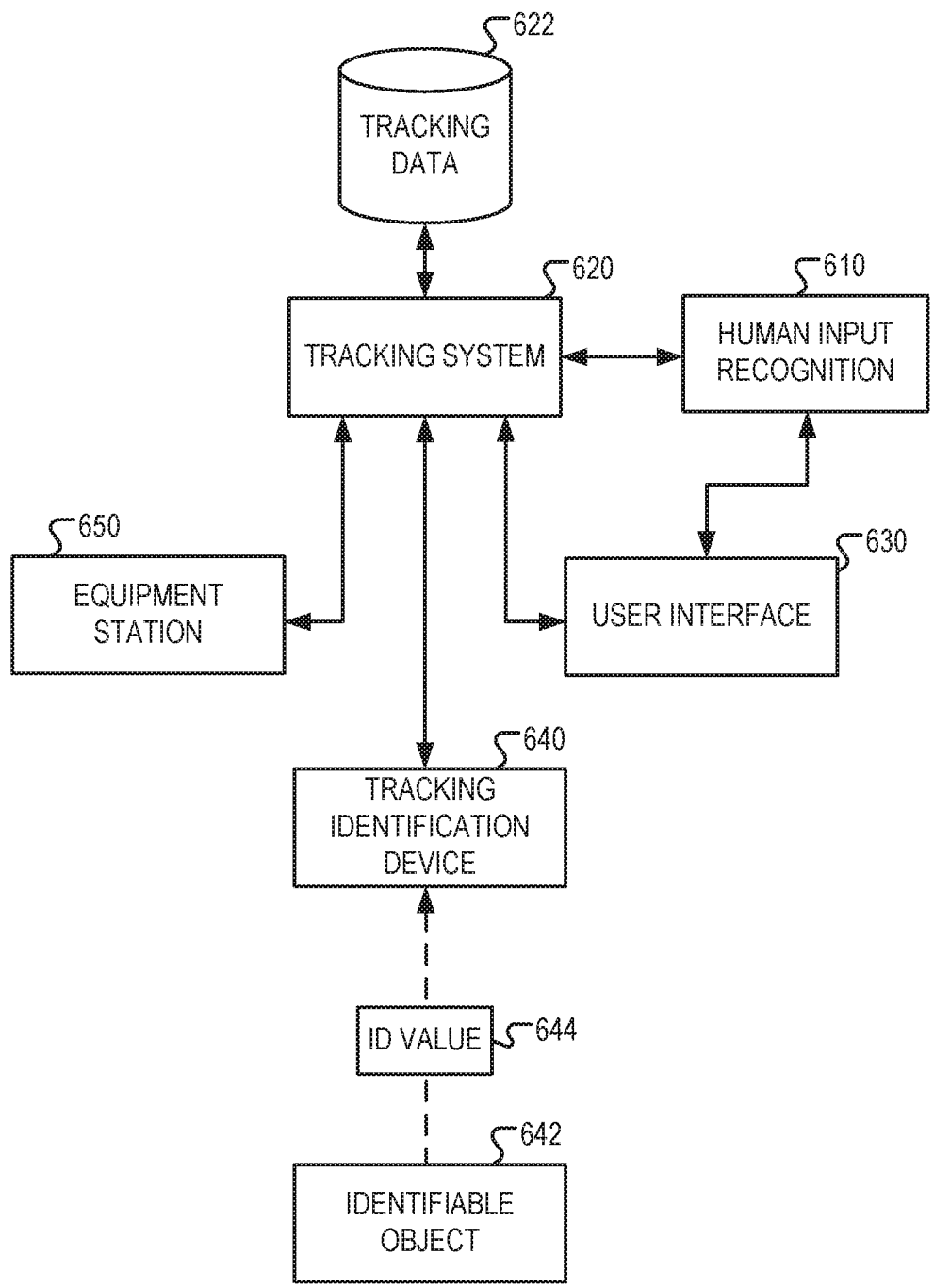
FIG. 6 is a block diagram of system components used to interface with a human input recognition component used with a tracking system in accordance with example embodiments.

FIG. 6 provides a block diagram illustrating the interaction between various devices and components in connection with use of a tracking workflow that is configured to obtain data from human input recognition using non-contact methods of human input. For example, the tracking workflow may be provided in connection with a medical device tracking workflow and device tracking system to manage the location, state (such as a contamination state), and other characteristics of a medical device.

As illustrated, a human input recognition component 610 is used to obtain non-contact human input in connection with prompts or user indications. The human input recognition component 610 is operably coupled to the tracking system 620. In another embodiment, the human input recognition component 610 may be directly included within the tracking system 620.

The tracking system 620 may be configured to log and otherwise track information related to an object or a set of objects, such as an identifiable object 642 (e.g., a reusable medical device). This information may be in the form of electronic or computer-readable tracking data maintained in a tracking data store 622.

The tracking system 620 is further operably coupled to one or more user interfaces such as user interface 630. For example, the user interface 630 may be provided in connection with an external display used to provide output and input for the tracking system 620. In one embodiment, the human input recognition component 610 is configured to directly provide active human input commands to the user interface 630. In another embodiment, the human input recognition component 610 is configured to indirectly provide active human input commands to the user interface 630 through communications facilitated by tracking system 620. In an alternative embodiment, active human input recognition commands are directly provided to the tracking system 620 and not communicated to the user interface 630, but rather the user interface 630 is used to obtain other types of input or serve as a backup input source.

The tracking system 620 is further operably coupled to one or more tracking identification devices such as tracking identification device 640. For example, the tracking identification device 640 may comprise a RFID reader or barcode reader used to obtain an identifier from one or more identifiable objects of interest. As illustrated in FIG. 6, the tracking identification device 640 obtains (e.g., reads) an identification value 644 (such as a global or locally unique identifier) from an identifiable object 642. The tracking system 620 is configured to obtain and store data for the identifiable object 642 based on the identification value 644.

In a medical device tracking system such as an endoscope tracking system, the identifiable object 642 may be an endoscope providing an identification value 644 in the form of a serial number or other identifier specific to the endoscope. Information that cannot be determined from identifying the endoscope with the tracking identification device 640, may be obtained through active human input using the human input recognition component 610.

The tracking system 620 is further operably coupled to one or more equipment stations such as equipment station 650. For example, in an endoscope reprocessing setting, the equipment station 650 may be an automatic endoscope reprocessor configured to perform automated cleaning procedures on an endoscope. As another example, the equipment station 650 may be a storage cabinet configured to store one or more uncontaminated endoscopes. Therefore, the tracking system 620 may be further configured to identify the location of a particular device among a plurality of equipment stations, and collect data from activities occurring at the plurality of equipment stations. In one embodiment, this collection of data may be performed responsive to the active input such as commands received with the human input recognition component 610.

The tracking system 620 may further be configured to log or track information obtained from the human input recognition component 610. For example, the particular active input commands issued from a human user may be used to verify the status of human operations at the equipment station 650, and such commands may need to be logged for further validation or auditing. Likewise, if a certain condition is observed by a human user at an equipment station 650, such as damage or malfunction of a particular device, then active human input such as verbalized observations or other inputted information may be associated with the identifiable object 642. The tracking system 620 may further coordinate the collection and use of tracking information for the identifiable object 642 for any number of purposes. For example, incident tracking related to the use of the identifiable object 642 may also be facilitated through use of the tracking system 620.

Figure 7:
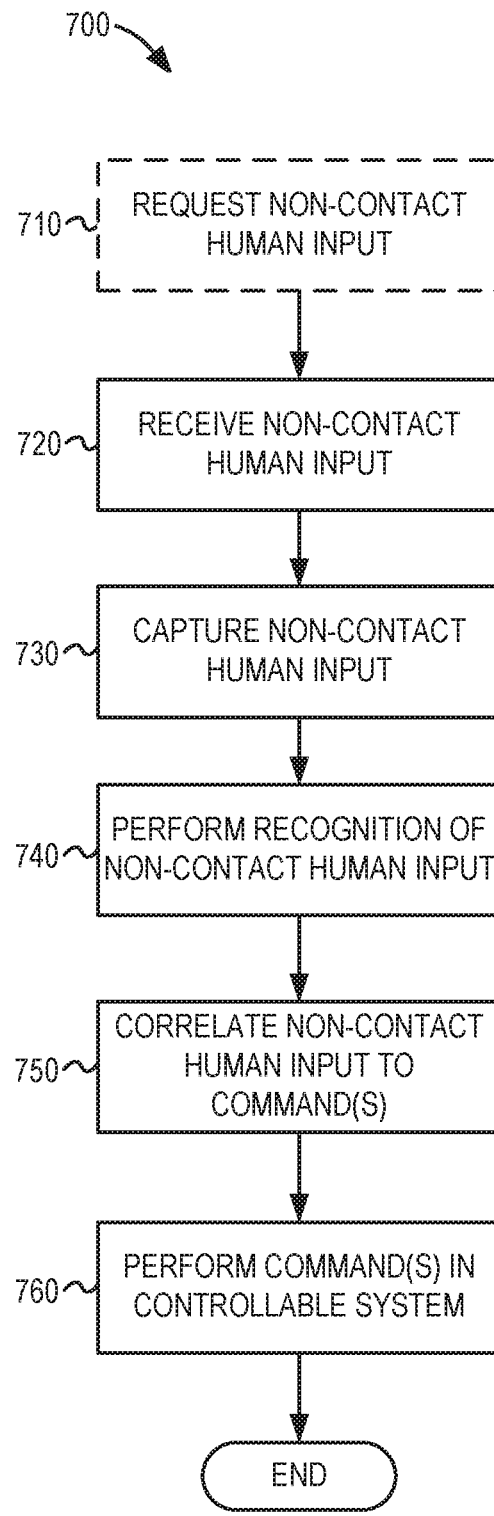
FIG. 7 illustrates a flowchart providing an overview of a method for performing commands responsive to human input recognition in accordance with example embodiments.

FIG. 7 illustrates a flowchart 700 providing an overview of a method for performing commands responsive to human input recognition in accordance with some embodiments. In some embodiments, certain non-contact human input may be requested by a device or system (operation 710) using one or more prompts for the non-contact human input. For example, this may include audio instructions or displayed instructions to prompt certain types or content of human input from a human user. Such a request for non-contact human input may be optional in some scenarios, however.

Further to the input capture and recognition techniques described herein, non-contact human input may be received (operation 720) and captured (operation 730). Various detection and recognition techniques may be performed upon the captured non-contact human input to conduct recognition (operation 740). The non-contact human input may be correlated with one or more commands (operation 750), to determine the one or more commands capable of performance upon a device, system, or other controllable system such as a computing system. Finally, the one or more commands may be performed within the controllable system (operation 760).

In a further embodiment, the active human input provided in connection with the recognition techniques described herein may also be used for any combination of identification, security, or authentication purposes. As one example, speech recognition may be combined with security voice recognition, to recognize the voice signature or otherwise identify the voice characteristics of a specific human user. A positive identification of the user of the system may be used to operate and authenticate to a secure system without requiring contact-based input such as a keyboard-provided user ID and password. Positive identification techniques also may be used to accept or filter certain commands or data inputs only from certain users or groups of users.

As another example, facial recognition may be combined with gesture-based input capture to identify a certain person based on the person's characteristics or a series of gestures performed by the person. Relevant characteristics may include basic characteristics such as an outline of a person, or more complex techniques such as biometric identification of a person's physical characteristics from facial feature recognition, iris or retinal identification, and the like.

Such security and authentication techniques may also be used in connection with user tracking in an object handling workflow, such as the cleaning or tracking workflows described herein, to track human interaction of a particular user with a particular object. For example, if multiple human users are interacting with a particular object throughout the workflow, the identification of the user during the human input detection may be stored or otherwise associated with workflow or tracking data. As another example, voice recognition or feature recognition of a particular human to identify the user may be useful to obtain input from a certain user in a multi-person environment, and to respond to active user input provided only by an authorized or recognized person.

Variations to the presently described input recognition techniques and input recognition devices may be provided. In particular, other types of non-contact active human input may be facilitated independently or in conjunction with the recognition techniques described herein. For example, an infrared or ultrasonic sensor may be used to capture active human input, such as by having two sensors with a first sensor configured to detect human movement above the sensor for a "pass" indication and a second sensor configured to detect human movement above the sensor for a "fail" indication. Various types of motion detector devices may also be used in conjunction with the presently described techniques and configurations to determine input or improve the accuracy of a human input recognition technique.

Although some of the preceding examples were provided with reference to endoscope processing and similar medical device cleaning settings, it will be understood that a variety of other uses may be applied in both medical and non-medical settings to prevent or reduce the potential of contamination. These settings may include the handling of hazardous materials in a various of scientific and industrial settings, such as the handling of objects contaminated with biological, chemical, or radioactive agents; the human control of systems and devices configured to process and clean potentially contaminated objects; and other settings involving human input that is obtained in connection with a contaminated object or human. Likewise, the preceding examples may also be applicable in clean room settings where the environment or particular objects are intended to remain in a clean state, and where human contact with substances or objects may cause contamination and is therefore intended to be minimized.

Techniques to detect the human input and perform recognition of the active human user input may be provided using any combination of software, hardware, device, and system configurations. For example, one or more computing systems may be configured to operate software configured to execute algorithms to detect non-contact human input, extract relevant data and commands using recognition of the non-contact human input, and utilize the data and commands in a user interface or computer-implemented process.

Figure 8:
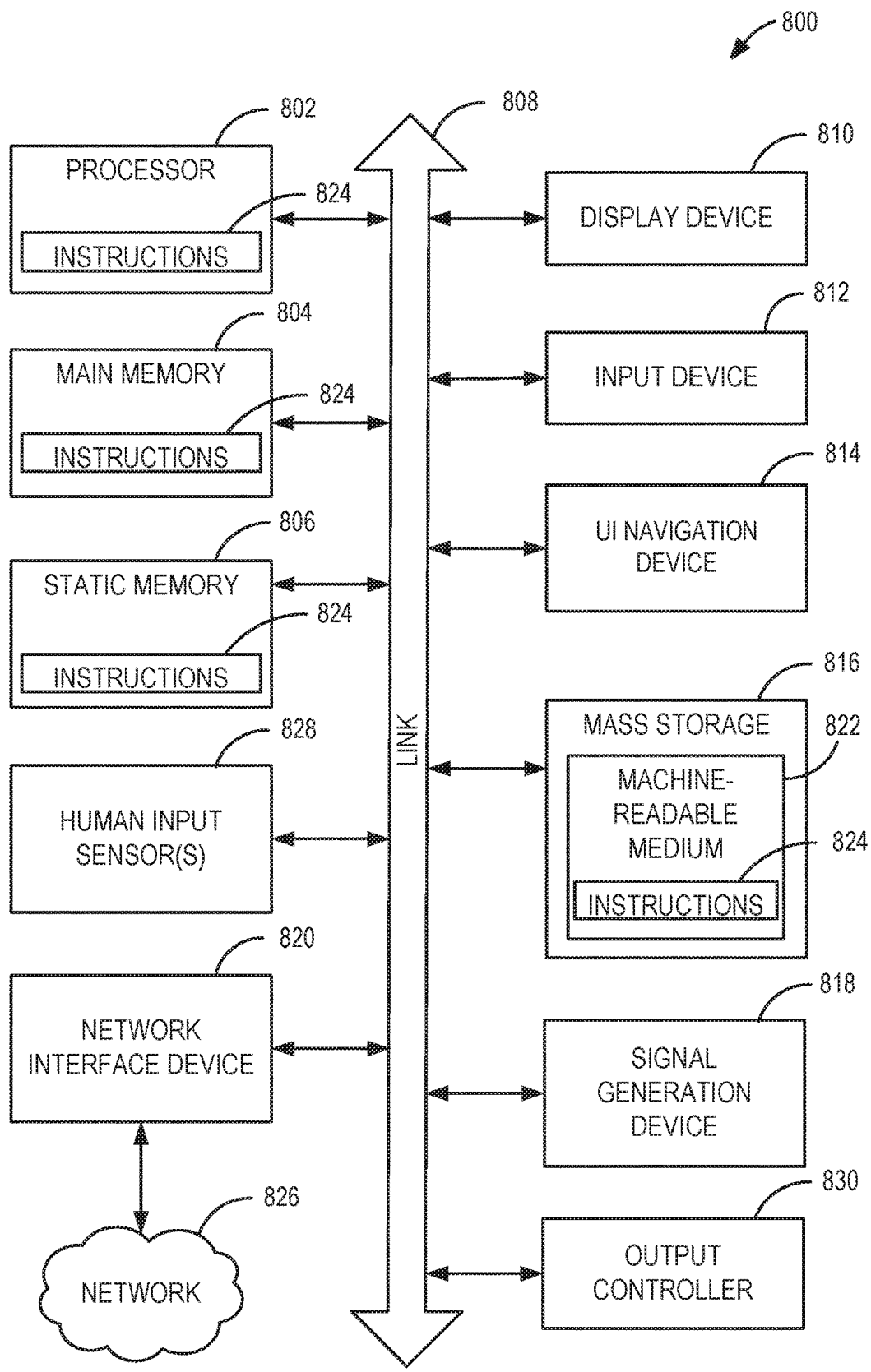
FIG. 8 is a block diagram of architecture for an example computing system used in accordance with example embodiments.

FIG. 8 is a block diagram illustrating an example computer system machine upon which any one or more of the user input recognition techniques herein discussed may be performed or facilitated by. Computer system 800 specifically may be used in connection with facilitating the operations of the cleaning workflow system, the device tracking system, or any other computing platform described or referred to herein. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a Personal Digital Assistant (PDA), a mobile telephone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

Example computer system 800 includes a processor 802 (e.g., a central processing unit (CPU), a graphics processing unit (GPU) or both), a main memory 804 and a static memory 806, which communicate with each other via a link 808 (e.g., an interlink, bus, etc.). The computer system 800 may further include a video display unit 810, an alphanumeric input device 812 (e.g., a keyboard), and a user interface (UI) navigation device 814 (e.g., a mouse). In one embodiment, the video display unit 810, input device 812 and UI navigation device 814 are a touch screen display. The computer system 800 may additionally include a storage device 816 (e.g., a drive unit), a signal generation device 818 (e.g., a speaker), and a network interface device 820 which may operably communicate with a communications network 826 using wired or wireless communications hardware. The computer system 800 may further include one or more human input sensors 828 configured to obtain non-contact human input in accordance with the human input recognition techniques described herein. The human input sensors 828 may include a camera, microphone, barcode reader, RFID reader, near field communications reader, or other sensor producing data for purposes of human input recognition. The computer system 800 may further include an output controller 830, such as a serial (e.g., universal serial bus (USB), parallel, or other wired or wireless (e.g., infrared (IR)) connection to communicate or control one or more peripheral devices (e.g., a printer, card reader, etc.).

The storage device 816 may include a machine-readable medium 822 on which is stored one or more sets of data structures or instructions 824 (e.g., software) embodying or utilized by any one or more of the methodologies or functions described herein. The instructions 824 may also reside, completely or at least partially, within the main memory 804, static memory 806, and/or within the processor 802 during execution thereof by the computer system 800, with the main memory 804, static memory 806, and the processor 802 also constituting machine-readable media.

While the machine-readable medium 822 is illustrated in an example embodiment to be a single medium, the term "machine-readable medium" may include a single medium or multiple media a centralized or distributed database, and/or associated caches and servers) that store the one or more instructions 824. The term "machine-readable medium" shall also be taken to include any tangible medium that is capable of storing, encoding or carrying instructions for execution by the computer system 800 and that cause the computer system 800 to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of well-known transfer protocols (e.g., frame relay, internes, protocol (IP), transmission control protocol (TCP), user datagram protocol (UDP), hypertext transfer protocol (HTTP)). Examples of communication networks include a local area network (LAN), wide area network (WAN), the Internet, mobile telephone networks, Plain Old Telephone (POTS) networks, and wireless data networks (e.g., Wi-Fi, 3G, and 4G LTE/LTE-A or WiMAX networks). The term "transmission medium" shall be taken to include any intangible medium that is capable of storing, encoding, or carrying instructions for execution by the computing system 800, and includes digital or analog communications signals or other intangible medium to facilitate communication of such software.

As an additional example, computing embodiments described herein may be implemented in one or a combination of hardware, firmware, and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media.

It should be understood that the functional units or capabilities described in this specification may have been referred to or labeled as components or modules, in order to more particularly emphasize their implementation independence. Component or modules may be implemented in any combination of hardware circuits, programmable hardware devices, or other discrete components. Components or modules may also be implemented in software for execution by various types of processors. An identified component or module of executable code may, for instance, comprise one or more physical or logical blocks of computer instructions, which may, for instance, be organized as an object, procedure, or function. Nevertheless, the executables of an identified component or module need not be physically located together, but may comprise disparate instructions stored in different locations which, when joined logically together, comprise the component or module and achieve the stated purpose for the component or module. Indeed, a component or module of executable code may be a single instruction, or many instructions, and may even be distributed over several different code segments, among different programs, and across several memory devices.

Similarly, operational data may be identified and illustrated herein within components or modules, and may be embodied in any suitable form and organized within any suitable type of data structure. The operational data may be collected as a single data set, or may be distributed over different locations including over different storage devices, and may exist, at least partially, merely as electronic signals on a system or network. The components or modules may be passive or active, including agents operable to perform desired functions.

Additional examples of the presently described method, system, and device embodiments include the following, non-limiting configurations. Each of the following non-limiting examples may stand on its own, or may be combined in any permutation or combination with any one or more of the other examples provided below or throughout the present disclosure.

Example 1 can include subject matter (such as an apparatus, a method, a means for performing acts, or a machine readable medium including instructions that, when performed by the machine, that can cause the machine to perform acts), for preventing contamination with use of non-contact human input, by: capturing human input in a contamination-sensitive environment, the human input provided for control of an input-controllable electronic system, and the human input provided by a form of non-contact human input; performing input recognition upon the captured human input; determining a command from the input recognition to perform in the input-controllable system; and performing the command in the input-controllable electronic system.

Example 2 can include, or can optionally be combined with the subject matter of Example 1, to optionally include the input-controllable electronic system including a computing device configured to perform the input recognition, and wherein the input recognition comprises one or more of: speech recognition, gesture recognition, facial recognition, or identifier recognition.

Example 3 can include, or can optionally be combined with the subject matter of one or any combination of Examples 1 or 2, to optionally include the human input being provided in response to a prompt from the computing device, and wherein determining the command includes matching a result of the input recognition to an option in the prompt from the computing device.

Example 4 can include, or can optionally be combined with the subject matter of one or any combination of Examples 1-3, to optionally include the prompt from the computing device being used to instruct a human user to provide a data value with the human input, the data value being specific to a status of a contaminated object in the contamination-sensitive environment.

Example 5 can include, or can optionally be combined with the subject matter of one or any combination of Examples 1-4, to include subject matter (such as an apparatus, a method, a means for performing acts, or a machine readable medium including instructions that, when performed by the machine, that can cause the machine to perform acts), for preventing contamination in connection with an object handling workflow, by: tracking a contamination status of an object within an object handling workflow used in a contamination-sensitive environment; collecting data related to the object at a plurality of stages of the object handling workflow; and recognizing non-contact human input provided by a human user in the contamination-sensitive environment during at least one of the plurality of stages of the object handling workflow, the recognized human input providing additional data related to the object for use in the object handling workflow.

Example 6 can include, or can optionally be combined with the subject matter of Example 5 to optionally include the additional data being provided from the recognized human input includes a command for control of the object handling workflow, and wherein the method further comprises performing an activity in the object handling workflow responsive to successfully recognizing the command from the non-contact human input.

Example 7 can include, or can optionally be combined with the subject matter of one or any combination of Examples 5 or 6 to optionally include the non-contact human input being verbal input provided from the human user, and wherein recognizing the non-contact human input includes performing speech recognition on a data capture of the verbal input.

Example 8 can include, or can optionally be combined with the subject matter of one or any combination of Examples 5-7 to optionally include the human input being gesture input provided from the human user, and wherein recognizing the non-contact human input includes performing gesture recognition on a data capture of the gesture input.

Example 9 can include, or can optionally be combined with the subject matter of one or any combination of Examples 5-8, to optionally include the human input being an identifier presented by the human user, and wherein recognizing the non-contact human input includes performing identifier recognition on a data capture of the identifier.

Example 10 can include, or can optionally be combined with the subject matter of one or any combination of Examples 5-9, to optionally include the identifier being one of: a barcode, a radio-frequency identification (RFID) identifier, or a near field communication identifier.

Example 11 can include, or can optionally be combined with the subject matter of one or any combination of Examples 5-10, to optionally include the non-contact human input being facial detection input provided from the human user, and wherein recognizing the non-contact human input includes performing facial detection recognition on a data capture of the facial detection input.

Example 12 can include, or can optionally be combined with the subject matter of one or any combination of Examples 5-11, to optionally include outputting one or more audio or visual indications at one or more stages of the object handling workflow to prompt the human user to provide the non-contact human input.

Example 13 can include, or can optionally be combined with the subject matter of one or any combination of Examples 5-12, to optionally include attempting positive identification of the human user from the non-contact human input to identify the human user as an authorized user to perform an activity within the object handling workflow.

Example 14 can include, or can optionally be combined with the subject matter of one or any combination of Examples 5-13, to optionally include attempting positive identification of the human user from the non-contact human input includes one or more of: attempting voice recognition of an audio sample captured from the non-contact human input; or attempting facial recognition of an image of the human captured from the non-contact human input.

Example 15 can include, or can optionally be combined with the subject matter of one or any combination of Examples 5-14, to optionally include the device being a medical device, wherein the object handling workflow is a medical device tracking workflow used for tracking a contamination status of the medical device.

Example 16 can include, or can optionally be combined with the subject matter of one or any combination of Examples 5-15, to optionally include the device being a medical device, wherein the object handling workflow is a medical device cleaning workflow used to decontaminate the medical device.

Example 17 can include, or can optionally be combined with the subject matter of one or any combination of Examples 5-16, to optionally include the medical device being an endoscope, wherein the object handling workflow is an endoscope cleaning workflow used for cleaning and reprocessing of the endoscope to remove contamination of the endoscope responsive to an endoscopy procedure using the endoscope.

Example 18 can include, or can optionally be combined with the subject matter of one or any combination of Examples 5-17, to optionally include the medical device cleaning workflow including a series of processing stages to enable disinfection of the medical device, the series of processing stages including: testing the medical device; performing manual cleaning upon the medical device; performing automated cleaning upon the medical device; and storing the medical device.

Example 19 can include, or can optionally be combined with the subject matter of one or any combination of Examples 5-18, to optionally include verifying a completion of each step in a determined order in the medical device cleaning workflow using the non-contact human input.

Example 20 can include, or can optionally be combined with the subject matter of one or any combination of Examples 5-19, to optionally include generating an error message responsive to failure of the completion of a step in the determined order in the medical device cleaning workflow.

Example 21 can include, or can optionally be combined with the subject matter of one or any combination of Examples 5-20, to optionally include tracking activities performed in the object handling workflow, including tracking the non-contact human input and activity performed responsive to the recognized human input.

Example 22 can include, or can optionally be combined with the subject matter of one or any combination of Examples 1-21 to include, subject matter (such as an apparatus, a method, a means for performing acts, or a machine readable medium including instructions that, when performed by the machine, that can cause the machine to perform acts), such as can include a computing device configuration, comprising: a processor; a human input sensor configured to detect a form of non-contact human input; and a memory unit, the memory unit providing a plurality of instructions, the instructions operable with the processor and the human input sensor, to: perform input recognition of the non-contact human input provided by a user and captured by the human input sensor at one or more stages of a medical device handling workflow; and correlate a result of the input recognition to a command for performance in the medical device handling workflow.

Example 23 can include, or can optionally be combined with the subject matter of Example 22, to optionally include the non-contact human input being provided by the user in response to a prompt generated by the computing device.

Example 24 can include, or can optionally be combined with the subject matter of one or any combination of Examples 22 or 23, to optionally include a human output device including a speaker; wherein the human input sensor includes a microphone; wherein the non-contact human input includes verbal input provided from a human user; and wherein the instructions are further operable with the processor, microphone, and speaker, to provide an audible prompt for the verbal input to the human user using the speaker, and to capture the verbal input from the human user using the microphone responsive to the audible prompt.

Example 25 can include, or can optionally be combined with the subject matter of one or any combination of Examples 22-24, to optionally include the non-contact human input being processed with at least one human input recognition technique to obtain detected commands and detected data values provided from a human user for use in the medical device handling workflow.

Example 26 can include, or can optionally be combined with the subject matter of one or any combination of Examples 1-25 to include, subject matter (such as an apparatus, a method, a means for performing acts, or a machine readable medium including instructions that, when performed by the machine, that can cause the machine to perform acts), of a medical device tracking system, comprising: a database configured to store a contamination status of a medical device; a user interface for interaction with an object tracking workflow, the object tracking workflow used for managing the contamination status of the medical device; and a human input recognition processing unit used for hands free interaction with the medical device tracking system during the object tracking workflow, the human input recognition processing unit configured for capturing the human input, processing the human input, and providing the human input for use in the object tracking workflow.

Example 27 can include, or can optionally be combined with the subject matter of Examples 26, to optionally include activities performed in connection with the medical device that occur in connection with steps of the object tracking workflow for cleaning and reprocessing the medical device for subsequent use.

Example 28 can include, or can optionally be combined with the subject matter of one or any combination of Examples 26 or 27, to optionally include the medical device being a multiple-use endoscope.

Example 29 can include, or can optionally be combined with the subject matter of one or any combination of Examples 1-28 to include, subject matter (such as an apparatus, a method, a means for performing acts, or a machine readable medium including instructions that, when performed by the machine, that can cause the machine to perform acts), configured for: tracking a medical device within a workflow; collecting data at one or more stages of the workflow; and performing input recognition upon non-contact human input provided by a human during at least one of the one or more stages of the workflow, the recognized non-contact human input providing data for the workflow.

Example 30 can include, or can optionally be combined with the subject matter of Example 29, to optionally include correlating a result of the input recognition to a command executable in the computing system for performance in the workflow; and performing the command in the computing system.

Example 31 can include, or can optionally be combined with the subject matter of one or any combination of Examples 29 or 30, to optionally include the input recognition including one or more of: speech recognition, gesture recognition, facial recognition, or identifier recognition.

Example 32 can include, or can optionally be combined with the subject matter of one or any combination of Examples 29-31, to optionally include the input recognition including speech recognition performed on speech from the human user captured with audio input.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A method for tracking cleaning operations in a scope handling workflow, comprising operations performed by an electronic system, with the operations comprising:
    identifying a stage of the scope handling workflow used for reprocessing an endoscope, wherein the scope handling workflow designates a cleaning activity to be performed on the endoscope at the identified stage of the scope handling workflow;
    capturing data for the endoscope during the identified stage of the scope handling workflow, based on non-contact human-machine input provided from a human user, wherein the captured data indicates a state of the cleaning activity that is selected by the human user via the non-contact human-machine input; and
    performing a command with the electronic system, based on the state of the cleaning activity, to cause a change in the scope handling workflow, wherein the command of the electronic system is performed in response to the human user providing the non-contact human-machine input, and wherein the non-contact human-machine input causes an update to data tracked for the scope handling workflow to indicate the change in the scope handling workflow.

2. The method of claim 1, the operations further comprising:
    obtaining a barcode or RFID identifier of the endoscope to identify the endoscope during the scope handling workflow, wherein the identifier indicates a serial number or unique identifier for tracking the endoscope.

3. The method of claim 1, wherein capturing the data for the endoscope comprises obtaining a barcode or RFID identifier corresponding to the cleaning activity, with the identifier indicating a respective state of the cleaning activity, and wherein the command is performed with the electronic system based on the state of the cleaning activity indicated by the identifier.

4. The method of claim 1, wherein the state of the cleaning activity indicates that a particular cleaning protocol has been followed by the human user during the reprocessing of the endoscope.

5. The method of claim 4, the operations further comprising:
    identifying the human user for performance of the particular cleaning protocol, wherein the identifying of the human user is performed based on at least one of: recognition of an identifier associated with the human user, facial recognition of a face of the human user, iris or retinal identification of an eye of the human user, or voice recognition of a voice sample captured from the human user;
    wherein the command is performed with the electronic system in response to a determination that the human user, as identified, is authorized to perform the command.

6. The method of claim 1, the operations further comprising:
    tracking the data for the scope handling workflow in a database, the database maintaining a contamination status of the endoscope and a state of respective cleaning activities performed on the endoscope.

7. The method of claim 1, the operations further comprising:
    tracking the command performed in the scope handling workflow, by maintaining a log that tracks the identified stage of the scope handling workflow and the state of the cleaning activity performed on the endoscope, wherein the log is accessible in connection with validation or auditing of performance of a plurality of commands in the scope handling workflow.

8. The method of claim 1, the operations further comprising:
    tracking a location of the endoscope during performance of the scope handling workflow, by maintaining a log that tracks: respective actions performed with the endoscope during the scope handling workflow, respective locations of the endoscope among a plurality of equipment stations, and respective activities occurring at the plurality of equipment stations.

9. The method of claim 1, the operations further comprising:
    outputting a prompt for input to the human user, in connection with the cleaning activity, via an output device operably coupled to the electronic system.

10. The method of claim 9, the operations further comprising:
    outputting, in response to capturing data for the endoscope, a first indication that corresponds to the state of the cleaning activity; and
    outputting, in response to performing the command, a second indication that corresponds to the change in the scope handling workflow;
    wherein the first and the second indication are output to the human user via an audio device or a display device.

11. The method of claim 9, the operations further comprising:
    capturing the non-contact human-machine input provided by the human user, in response to the prompt, wherein the non-contact human-machine input is an input provided from among: audio input, gesture input, or machine-readable identifier input types, to an input device, and wherein the command of the electronic system is further performed based on recognition on the non-contact human-machine input.

12. The method of claim 11, wherein the prompt requests the human user to provide the non-contact human-machine input based on the identified stage of the scope handling workflow.

13. The method of claim 1, wherein the electronic system is in communication with an automated cleaning machine, and wherein the command controls an action to be conducted by the automated cleaning machine as part of cleaning activities performed on the endoscope in the scope handling workflow.

14. The method of claim 1, wherein the state of the cleaning activity is indicated with:
   a pass result, wherein the change in the scope handling workflow includes proceeding to a next stage in response to the pass result; or
   a fail result, wherein the change in the scope handling workflow includes conducting a remedial action for the identified stage in response to the fail result.

15. An electronic system adapted for tracking cleaning operations in a scope handling workflow, comprising:
   a computer comprising processing circuitry to execute instructions to:
      identify a stage of the scope handling workflow used for reprocessing an endoscope, wherein the scope handling workflow designates a cleaning activity to be performed on the endoscope at the identified stage of the scope handling workflow;
      capture data for the endoscope during the identified stage of the scope handling workflow, based on non-contact human-machine input provided from a human user, wherein the captured data indicates a state of the cleaning activity that is selected by the human user via the non-contact human-machine input; and
      perform a command with the electronic system, based on the state of the cleaning activity, to cause a change in the scope handling workflow, wherein the command of the electronic system is performed in response to the human user providing the non-contact human-machine input, and wherein the non-contact human-machine input causes an update to data tracked for the scope handling workflow that indicates the change in the scope handling workflow.

16. The electronic system of claim 15, further comprising:
   an input device to capture the non-contact human-machine input provided by the human user, the input device configured to be operably coupled to the computer, wherein the non-contact human-machine input is an input provided by the human user from among: audio input, gesture input, or machine-readable identifier input types, and wherein the command of the electronic system is determined based on recognition on the non-contact human-machine input.

17. The electronic system of claim 15, further comprising:
   an identifier reader to read an identifier during the identified stage of the scope handling workflow, the identifier reader configured to be operably coupled to the computer, wherein the identifier reader is configured to obtain a barcode or RFID identifier to:
      identify the endoscope during the scope handling workflow, wherein the identifier indicates a serial number or unique identifier for tracking the endoscope; or
      identify a result for the state of the cleaning activity, the identifier being associated with a respective result, wherein the command is performed based on the result for the state of the cleaning activity.

18. The electronic system of claim 15, further comprising:
   an output device to output a prompt to the human user, the output device configured to be operably coupled to the computer, wherein the prompt is output in connection with the cleaning activity.

19. The electronic system of claim 18, the processing circuitry to execute further instructions to:
   capture the non-contact human-machine input provided by the human user, wherein the non-contact human-machine input is an input provided from among: audio input, gesture input, or machine-readable identifier input types, to an input device, and wherein the command of the electronic system is determined from recognition on the non-contact human-machine input;
   wherein the prompt requests the human user to provide the non-contact human-machine input based on the identified stage of the scope handling workflow.

20. The electronic system of claim 15, the processing circuitry to execute further instructions to:
   track the command performed in the scope handling workflow, by maintaining a log that tracks the identified stage of the scope handling workflow and the state of the cleaning activity performed on the endoscope, and wherein the log is accessible in connection with validation or auditing of performance of a plurality of commands in the scope handling workflow; and
   track a location of the endoscope during performance of the scope handling workflow, by maintaining a log that tracks: respective actions performed with the endoscope during the scope handling workflow, respective locations of the endoscope among a plurality of equipment stations, and respective activities occurring at the plurality of equipment stations.

21. The electronic system of claim 15, the processing circuitry to execute further instructions to:
   track the data for the scope handling workflow in a database, the database maintaining a contamination status of the endoscope and a state of respective cleaning activities performed on the endoscope;
   wherein the state of the respective cleaning activities are used to track whether cleaning protocols have been followed by the human user during the reprocessing of the endoscope.

22. At least one non-transitory machine-readable storage medium, comprising a plurality of instructions adapted for tracking cleaning operations in a scope handling workflow, wherein the instructions, responsive to being executed with processor circuitry of an electronic system, cause the processor circuitry to perform operations that:
   identify a stage of the scope handling workflow used for reprocessing an endoscope, wherein the scope handling workflow designates a cleaning activity to be performed on the endoscope at the identified stage of the scope handling workflow;
   capture data for the endoscope during the identified stage of the scope handling workflow, based on non-contact human-machine input provided from a human user, wherein the captured data indicates a state of the cleaning activity that is selected by the human user via the non-contact human-machine input; and
   perform a command with the electronic system, based on the state of the cleaning activity, to cause a change in the scope handling workflow, wherein the command of the electronic system is performed in response to the human user providing the non-contact human-machine input, and wherein the non-contact human-machine input causes an update to data tracked for the scope handling workflow to indicate the change in the scone handling workflow.

23. The machine-readable storage medium of claim 22, the instructions further to cause operations that:
capture non-contact human-machine input provided by the human user, wherein the non-contact human-machine input is an input provided by the human user from among: audio input, gesture input, or machine-readable identifier input types, to an input device, and wherein the command of the electronic system is determined from recognition on the non-contact human-machine input;
cause output of a prompt that requests the human user to provide the non-contact human-machine input based on the identified stage of the scope handling workflow.

24. The machine-readable storage medium of claim 22, the instructions further to cause operations that:
track the command performed in the scope handling workflow, by maintaining a log that tracks the identified stage of the scope handling workflow and the state of the cleaning activity performed on the endoscope, and wherein the log is accessible in connection with validation or auditing of performance of a plurality of commands in the scope handling workflow; and
track a location of the endoscope during performance of the scope handling workflow, by maintaining a log that tracks: respective actions performed with the endoscope during the scope handling workflow, respective locations of the endoscope among a plurality of equipment stations, and respective activities occurring at the plurality of equipment stations.

25. The machine-readable storage medium of claim 22, the instructions further to cause operations that:
track the data for the scope handling workflow in a database, the database maintaining a contamination status of the endoscope and a state of respective cleaning activities performed on the endoscope;
wherein the state of the respective cleaning activities are used to track whether cleaning protocols have been followed by the human user during the reprocessing of the endoscope.

\* \* \* \* \*